(12) United States Patent
Ahmed

(10) Patent No.: US 8,343,139 B2
(45) Date of Patent: Jan. 1, 2013

(54) PORTABLE PRESSURE RELIEF SYSTEM AND METHODS

(76) Inventor: A. Mateen Ahmed, Rancho Cucamonga, CA (US)

(*) Notice: Subject to any disclaimer, the term of this patent is extended or adjusted under 35 U.S.C. 154(b) by 767 days.

(21) Appl. No.: 11/925,418

(22) Filed: Oct. 26, 2007

(65) Prior Publication Data

US 2008/0114337 A1     May 15, 2008

Related U.S. Application Data

(63) Continuation of application No. 10/306,178, filed on Nov. 27, 2002, now abandoned.

(51) Int. Cl.
     *A61M 27/00*      (2006.01)
(52) U.S. Cl. ............ 604/541; 604/7; 604/8; 604/9; 604/10; 604/27; 604/30; 604/264; 604/167.03; 604/317; 604/323; 604/325; 604/327
(58) Field of Classification Search ............... 604/6.16, 604/7–10, 27, 30, 264, 167.03, 317, 323, 604/325, 327
See application file for complete search history.

(56) References Cited

U.S. PATENT DOCUMENTS

| | | | |
|---|---|---|---|
| 3,663,965 A | 5/1972 | Lee, Jr. et al. | |
| 3,957,050 A | 5/1976 | Hines, Jr. | |
| 4,328,813 A | 5/1982 | Ray | |
| 4,709,702 A | 12/1987 | Sherwin | |
| 4,988,093 A | 1/1991 | Forrest et al. | |
| 5,071,408 A | 12/1991 | Ahmed | |
| 5,464,446 A | 11/1995 | Dreessen et al. | |
| 5,683,357 A | 11/1997 | Magram | |
| 5,743,869 A | 4/1998 | Ahmed | |
| 5,772,625 A | 6/1998 | Krueger et al. | |
| 5,865,842 A | 2/1999 | Knuth et al. | |
| 5,928,182 A | 7/1999 | Kraus et al. | |
| 6,210,346 B1 | 4/2001 | Hall et al. | |
| 6,283,934 B1 | 9/2001 | Borgesen | |
| 2004/0049134 A1 | 3/2004 | Tosaya | |

OTHER PUBLICATIONS

Hardy's Textbook of Surgery, 5 pages, 1980.
Final Office Action in U.S. Appl. No. 10/306,178, Aug. 2007.
A. Mateen Ahmed Dissertation Dec. 1970.

*Primary Examiner* — Michele M Kidwell
*Assistant Examiner* — Ilya Treyger
(74) *Attorney, Agent, or Firm* — John J. Connors; Connors & Assoc

(57) ABSTRACT

A portable systems release fluid pressure with a cavity within a patient. These systems include a drainage catheter, a pressure-responsive one-way valve, and a fluid reservoir all adapted to be mounted in proximity to the cavity being drained. One system in particular is used in relieving intracranial pressure. This intracranial pressure relief system may include a headband to which are mounted the one-way valve and reservoir. The drainage catheter may have mounted thereon a cranium seal formed of a soft material that contacts the inner wall of a cranium bore hole. The cranium seal may have threads to facilitate advancement into the bore hole.

10 Claims, 7 Drawing Sheets

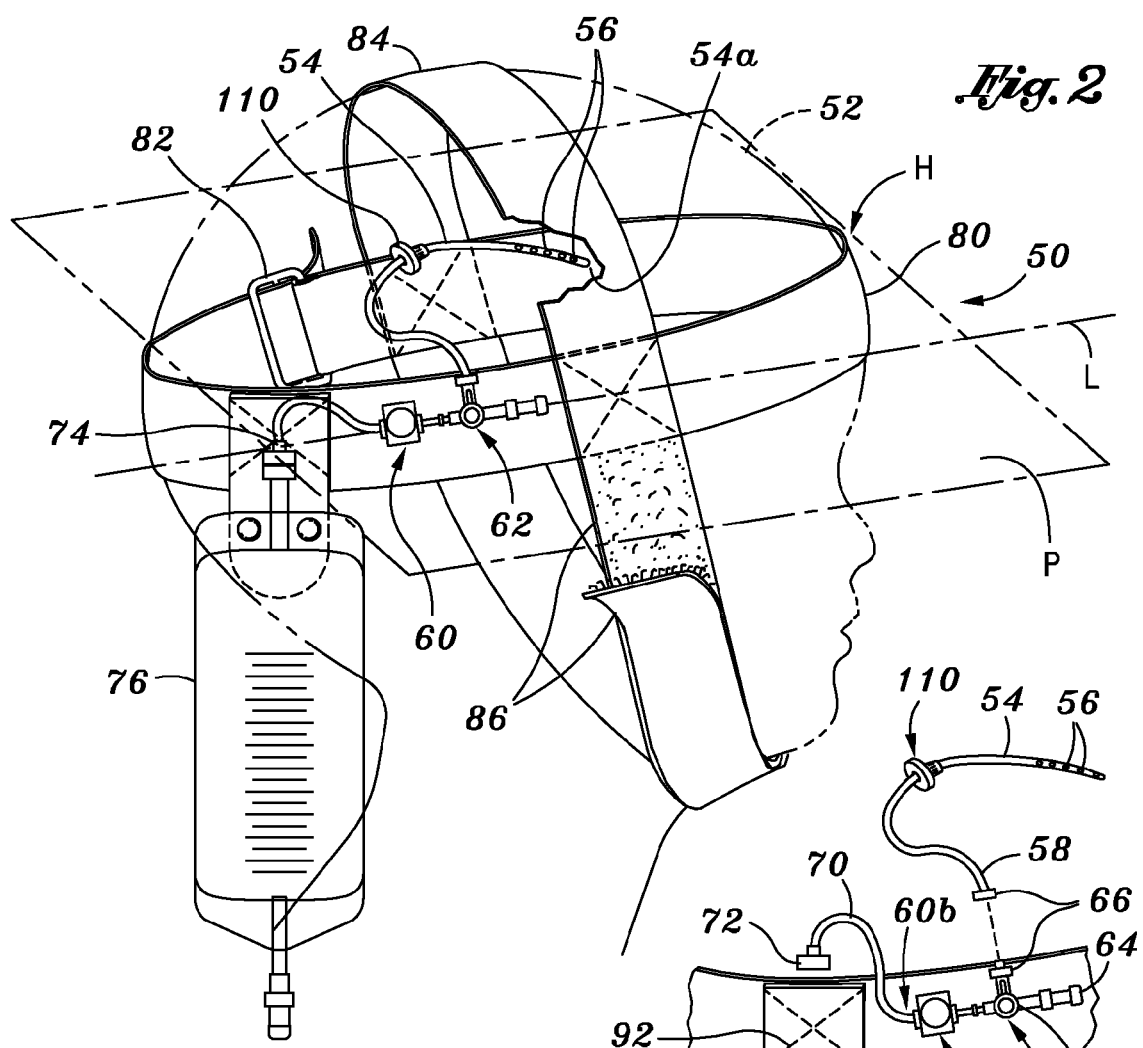
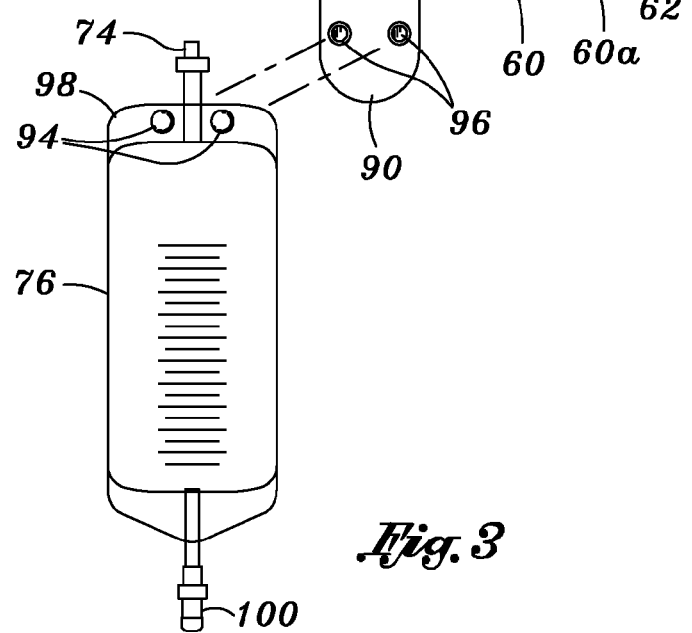

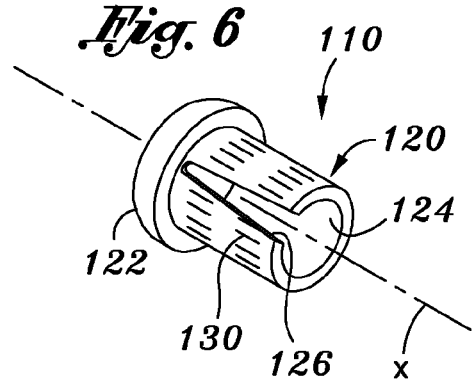
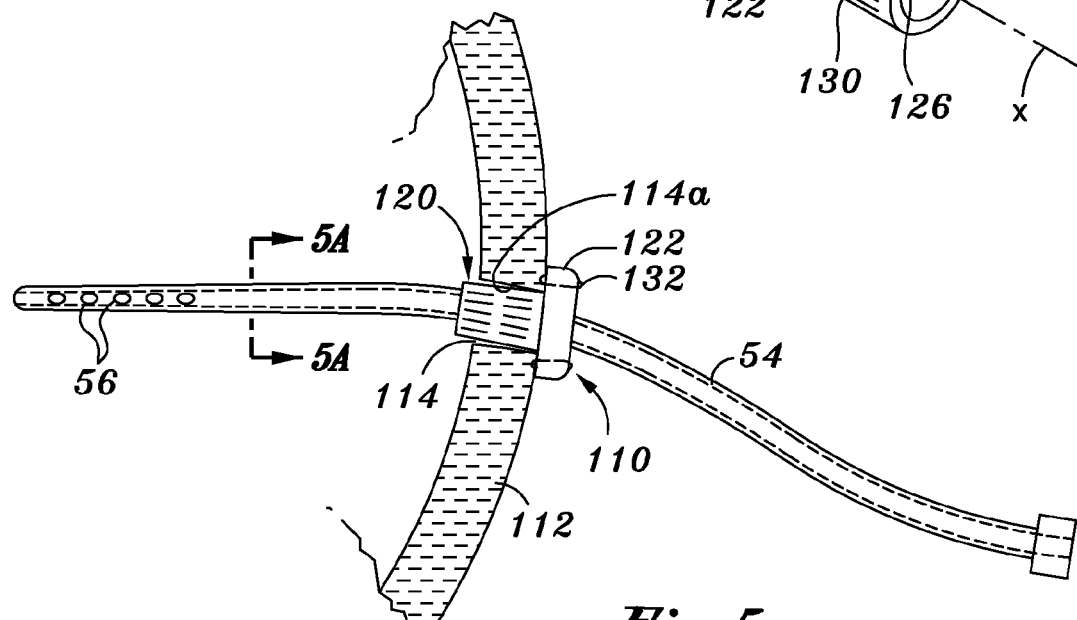
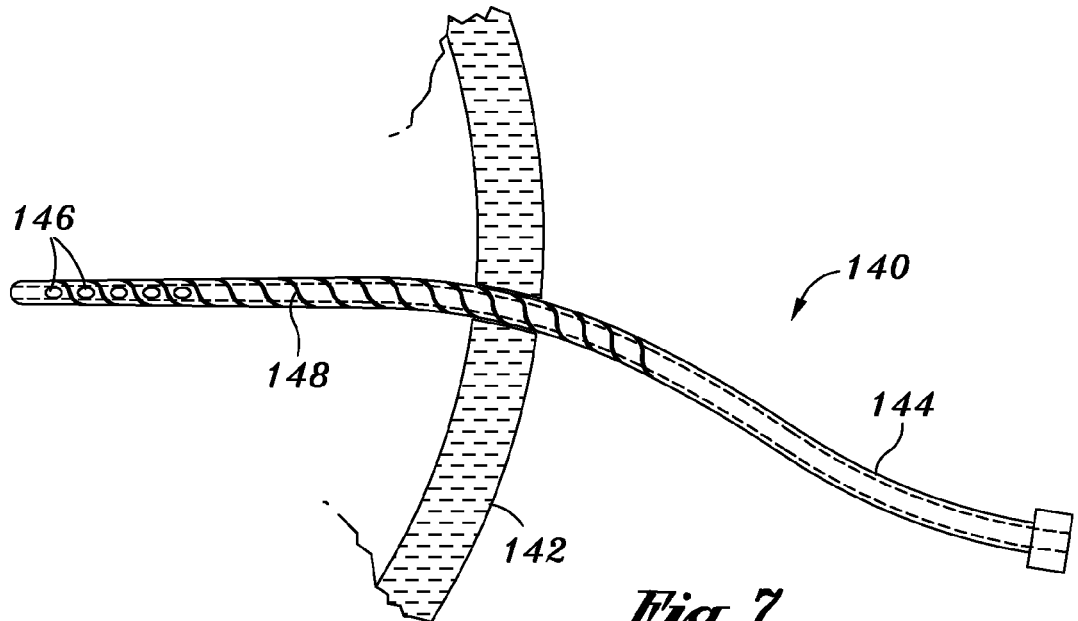

PORTABLE PRESSURE RELIEF SYSTEM AND METHODS

INCORPORATION BY REFERENCE

This application is a continuation application of U.S. application Ser. No. 10/306,178, entitled "PORTABLE PRESSURE RELIEF SYSTEM & METHODS," filed Nov. 27, 2002 now abandoned. Applicant incorporates herein by reference any and all U.S. patents, U.S. patent applications, and other documents cited or referred to in this application or cited or referred to in the U.S. patents and U.S. patent applications incorporated herein by reference.

DEFINITIONS

The words "comprising," "having," and "including," and other forms thereof, are intended to be equivalent in meaning and be open ended in that an item or items following any one of these words is not meant to be an exhaustive listing of such item or items, or meant to be limited to only the listed item or items.

BACKGROUND OF INVENTION

Frequently it is necessary to drain fluids, particularly liquids, from various cavities in the body. For example, hydrocephalus arises when the outflow of cerebrospinal fluid (CSF) is obstructed, which collects in the ventricles of the brain and produces an increase in the intracranial pressure. Left untreated, hydrocephalus can result in serious medical conditions, including subdural hematoma, compression of the brain tissue, and impaired blood flow. Excess intracranial pressure produces symptoms such as walking or gait problems, incontinence, dizziness, and others. Hemhorrages and other causes also may result in an increase intracranial pressure and manifestation of the same symptoms. Other cavities in the body also may collect fluid and cause excessive internal pressure. Once diagnosed, the treatment is to eliminate the excess pressure by draining whenever fluid is causing it from within the body cavity.

SUMMARY OF INVENTION

This invention, with its several desirable features, is summarized in the CLAIMS that follow. After reading the following section entitled "DETAILED DESCRIPTION OF SOME EMBODIMENTS OF THIS INVENTION," one will understand how the features of this invention provide its benefits. The benefits of this invention include, but are not limited to: reduced costs associated with care giving for patients requiring drainage of fluids, convenience of use and enhanced mobility of for patients requiring drainage of fluids, avoidance of catheter blockage, and enhanced patient mobility.

Without limiting the scope of this invention as expressed by the claims that follow, some, but not all, of its features are:

One, this invention comprises a portable system for relieving fluid pressure from a body cavity of a patient. It includes a drainage catheter for insertion into the body cavity. A first portion of the drainage catheter may be at least 4 inches in length for insertion into the cavity and a second portion that extends from the cavity.

Two, the invention may include a one-way pressure-responsive valve with an inlet in fluid communication with an outlet of the drainage catheter to permit pressure-regulated flow of fluid from the body cavity through the catheter. The pressure-responsive valve has an outlet that is at substantially atmospheric pressure and an inlet inserted into the body cavity and at the pressure within the body cavity. The valve opens and closes automatically in response to a changing differential in pressure between the inlet and outlet. The valve opens when the differential between atmospheric pressure and the pressure within the body cavity exceeds a predetermined difference and closes when this differential is less than this predetermined difference. In one embodiment, the pressure-responsive valve has a pair of membrane members that are in tension and form a slit opening that is normally closed. At a predetermined difference, the valve opens and fluid flows between the membrane members and forces the membrane members apart, to open the slit opening and allow the fluid to flow through the valve until predetermined difference is no longer present and the valve closes automatically.

Three, a reservoir may have an inlet in fluid communication with an outlet of the pressure-responsive valve so as to receive the fluid that passes therethrough. The outlet of the catheter, the inlet and outlet of the valve, and the inlet of the reservoir optimally are nearby each other so that there is essentially no hydrostatic pressure in the system affecting to flow of fluid from the body cavity. The distance between the outlet of the valve and the inlet of the reservoir typically is no greater than about 3 inches. The drainage catheter may have a distal end with drainage apertures therein, and this distal end of the drainage catheter, reservoir inlet, and pressure-responsive valve are at substantially the same height. In one embodiment, the outlet of the catheter, the inlet and outlet of the valve, and the inlet of the reservoir are substantially in a common plane.

Four, the drainage catheter, pressure-responsive valve, and reservoir may be connected to a mounting member that is adapted to be detachably coupled to the patient nearby the body cavity. In one embodiment, the drainage catheter, pressure-responsive valve, and reservoir are connected to a mounting member that is adapted to be detachably coupled to the head or cranium of the patient. The drainage catheter has a first end adapted to be inserted into a cavity in the cranium and a second end that is external to the cranium. The headband may include a first component sized to fit around the circumference of the patient's head, and a second component connected by opposed ends thereof to the first component and sized to fit over the top of the patient's head. The first component may be adjustable to different patient head circumferences. The headband may include a releasable chin strap to permit easy removal of the system. The headband may comprises at least partially hollow member that functions as the reservoir. The hollow member may be hoop-shaped. The reservoir may be detachably connected to the headband, for example, by a snap-type connector.

In this one embodiment, a connector adapted to be attached to the cranium holds the first end of the catheter in position in the cavity. This connector is also a feature of this invention, preventing leakage of fluid past it, so that essentially all the fluid flowing from the cavity passes through the catheter with essentially no fluid bypassing the catheter and flowing around the connector. The outlet of the pressure-responsive valve is attached so as to receive the fluid. The connector may be integral with the catheter and may include a thread element on an external surface of the catheter at or nearby the outlet end of the catheter. The connector fits snugly into a hole in the cranium to prevent any substantial leakage of fluid past the connector, and it may have a passageway therein through which the drainage catheter extends so that the outlet end of the catheter is external to the cranium. The passageway may be formed by a substantially cylindrical wall member with a cleft therein. Typically, the connector may have a body with external threads thereon enabling the connector to be screwed into the hole. This body is made of a material that deforms upon compression and has a substantially truncated conical shape sized to fit into the hole and compress as the connector is screwed to the hole. Such a connector provides a substantially fluid tight seal between the hole and the body, with the passageway being constricted as connector is screwed into the hole to provide a substantially fluid tight seal between the catheter and the passageway. In one embodiment, the body may have an enlarged head that acts as a stop adapted to bear against an external portion of the cranium surrounding the hole. The enlarged head may have at least one suture orifice therein to enable the connector to be sutured to the cranium to prevent movement of the connector within the hole after insertion into the hole.

This invention also includes a self-sealing catheter for insertion through a bore hole in a cranium of a patient. It comprises an elongated tubular catheter body sized to fit through the bore hole in the cranium and a sealing member mounted on the exterior of the catheter body made of a material that deforms upon insertion into the bore hole. The sealing member may have along at least a portion thereof an outer diameter larger than the bore hole to provide a substantially fluid tight seal between said bore hole and the sealing member upon insertion of the catheter into the bore hole. The sealing member may include a thread element that facilitates advancement into the bore hole. This thread element may comprise a helical bead formed on the exterior of the catheter body. The helical bead may be formed of silicone. Alternately, the sealing member may comprise a generally tubular sleeve having a narrow passageway that fits snugly around the catheter body and an enlarged head sized larger than the bore hole. An exterior surface of the tubular sleeve may be conical, having a narrow distal end and threads are formed on the exterior surface. The tubular sleeve may have a cleft that permits the sleeve to constrict upon insertion into the bore hole. The tubular catheter body may be moveable axial within the passageway prior to screwing the threaded element into the hole.

These features are not listed in any rank order nor is this list intended to be exhaustive.

This invention also includes methods for relieving fluid pressure resulting from fluid collecting within a body cavity. In these methods, a hole provides access to the cavity and the fluid is drained from the cavity by inserting a drainage catheter through the hole so that a distal end is lodged within the cavity and a proximal end extends from the cavity. The proximal end has a one-way pressure-responsive valve thereat with an outlet and an inlet in fluid communication with the drainage catheter to permit pressure-regulated flow of fluid from the cavity through the outlet of the valve. The fluid that passes through the valve is collected in a reservoir with an inlet in communication with the outlet of the valve. The proximal end of the catheter, the inlet and outlet of the valve, and the inlet of the reservoir are positioned nearby each other so that there is essentially no hydrostatic pressure affecting to flow of fluid from the cavity of a patient. Typically, the distance between the outlet of the valve and the inlet of the reservoir is no greater than 3 inches. Typically, the proximal end of the catheter, the inlet and outlet of the valve, and the inlet of the reservoir are at substantially the same height.

One method is specific for collecting fluid within a cavity formed at least in part by the ventricle walls of the brain enclosed within the cranium of a patient. A hole is formed in the cranium to provide access to the cavity and a plug-type connector sized to fit snugly in the hole to prevent any substantial leakage of fluid past the connector. The connector may have a passageway therein. An elongated drainage catheter passes through the passageway so that a first end of the catheter is seated within the cavity and a second end of the catheter is external to the cranium. The first end may have at least one drainage aperture therein. Typically, the drainage catheter fits snug within the passageway to prevent any substantial leakage of between the catheter and the passageway. The flow of fluid from the cavity is controlled so that the fluid pressure within cavity is maintained at a level that prevents the ventricle walls form making substantial contact with the drainage apertures. In one embodiment, a connector is used of the type discussed above.

DESCRIPTION OF DRAWINGS

Some embodiments of this invention, illustrating all its features, will now be discussed in detail. These embodiments depict the novel and non-obvious drainage system and methods of this invention as shown in the accompanying drawings, which are for illustrative purposes only. These drawings includes the following figures (Figs.), with like numerals indicating like parts:

FIG. 2 is a perspective view of an external intracranial drainage system of the present invention mounted on the head of a patient (shown in phantom);

FIG. 3 is a perspective view of the drainage system of FIG. 2 with the reservoir disconnected;

FIG. 5 is a partial sectional view of a drainage catheter of the system of FIG. 2 inserted through a bore hole in the cranium;

FIG. 5A is a cross-sectional view through the drainage catheter taken along line 5A-5A of FIG. 5;

FIG. 6 is a perspective view of a cranium connector or seal that mounts on the catheter of FIG. 5;

FIG. 7 is a partial sectional view of an alternative drainage catheter for use in the system of FIG. 2 inserted through a bore hole in the cranium;

PRIOR ART

Treatment of Hydrocephalus

The treatment of hydrocephalus aims to reduce the intracranial pressure to normal, physiological values and thereby also reduce the amount of CSF towards normal, physiological values. Typically, CSF is drained from the ventricular system to another resorption site, bypassing the pathological obstruction by use of a CSF shunt. The most suitable diversion sites for CSF have been found to be the right atrium of the heart and the peritoneal cavity.

Generally, fluid shunt systems include a valve mechanism to hinder retrograde flow in the drainage system which could occur due to pressure differences between the intracranial cavity and the resorption site, e.g. in connection with increased chest and/or abdominal pressure in connection with e.g cough or defecation. One shunt system includes a ventricular catheter inserted into a ventricle of the brain, a peritoneal catheter inserted into the peritoneal region for discharge of the fluid, and a valve mechanism therebetween. Exemplary shunt systems include U.S. Pat. No. 5,928,182 to Kraus, et al. The valve and catheters of such systems are typically attached to or implanted under the patient's scalp and left in place for significant periods.

Under certain circumstances, it is desirable to treat hydrocephalus by draining the excess fluid from the ventricles of the brain to a collection receptacle that is external to the body. This is typically the case of surgically induced hydrocephalus which may be only a temporary problem and would not require a totally implanted shunting system. In such a case, an external shunt or drainage system is desirable. One such system is disclosed in U.S. Pat. No. 5,772,625 to Krueger, et al.

External intracranial fluid drainage involves drilling a bore hole through the cranium and inserting a drainage catheter to the affected location. The drainage catheter has multiple apertures on its distal end through which the fluid automatically drains due to its excess pressure, or due to a siphoning effect. Sometimes the drainage catheter remains in place for extended periods of time so as to relieve pressure as it builds up. Typically, the amount and timing of fluid drainage is regulated by controlling the pressure differential between the proximal and distal ends of the catheter. An incorrect pressure differential results either in too much fluid drainage or inadequate drainage. The proper pressure differential permits fluid drainage only when the pressure within the cranium builds to an unacceptable level, and that pressure is preferably accounted for when calibrating the drainage system.

Figure 1:
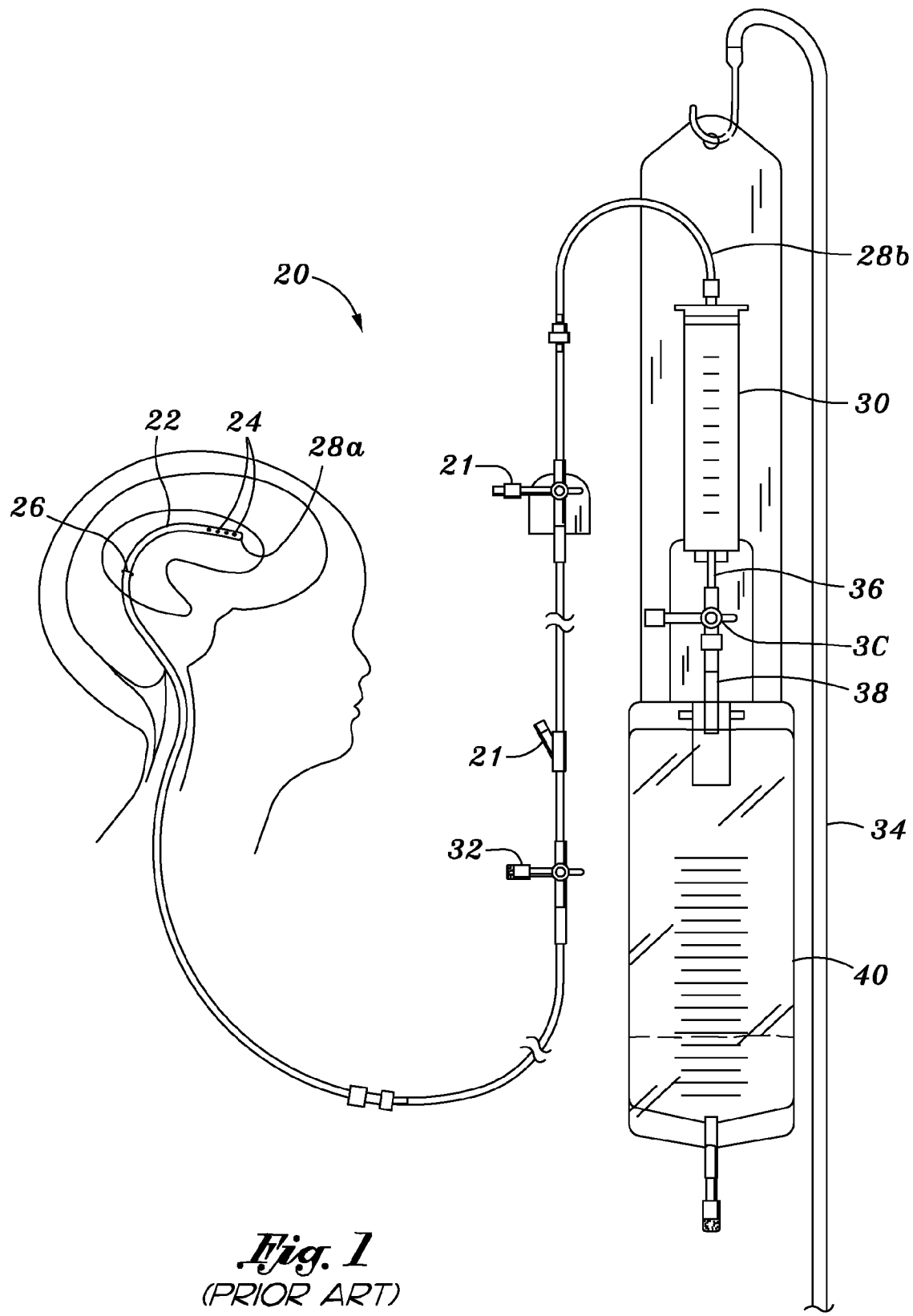
FIG. 1 is a schematic illustration of a prior art external intracranial drainage system having a drainage catheter inserted into the cranium of the patient (shown in phantom)
Figure 4:
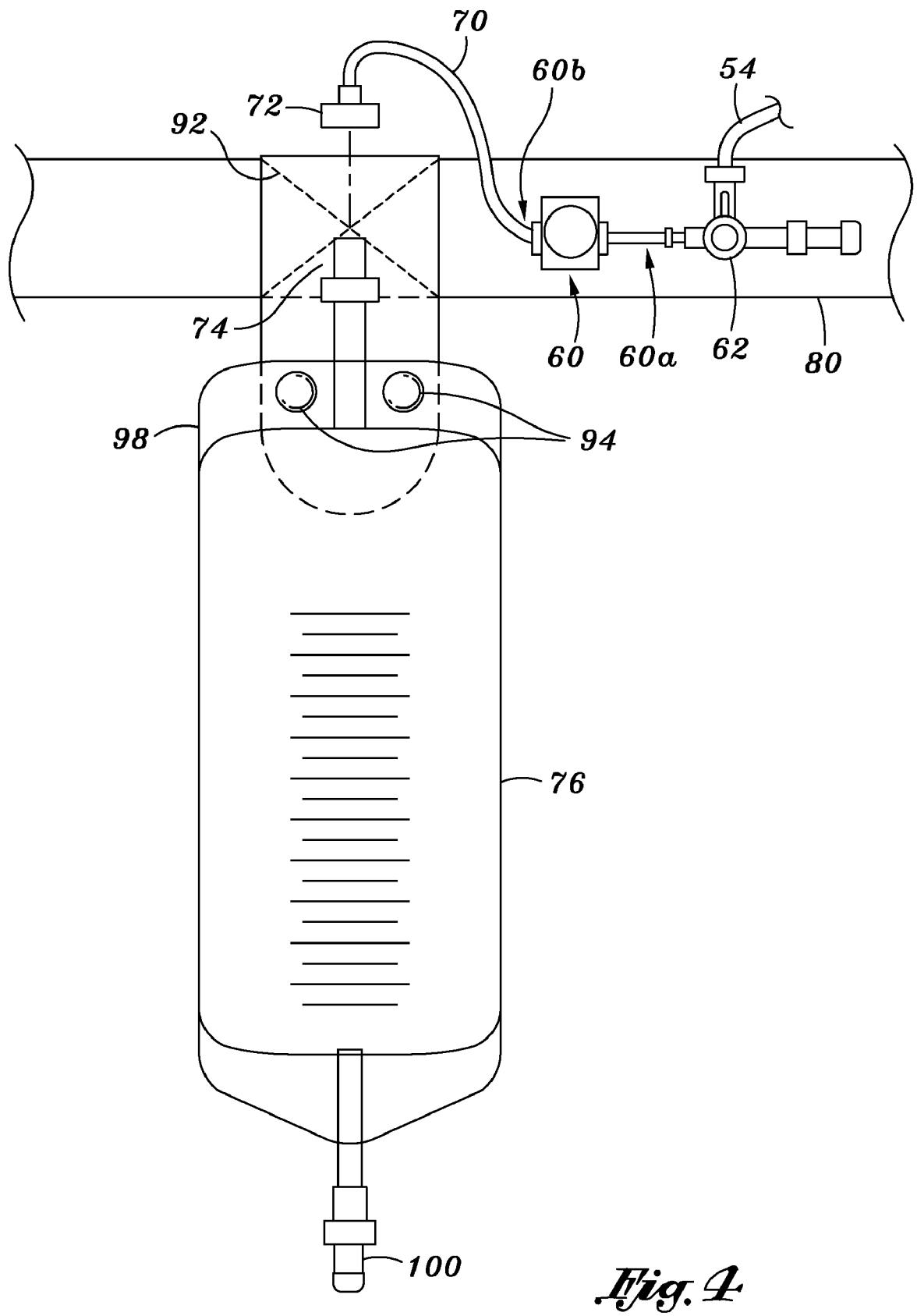
FIG. 4 is a side elevational view of a portion of the drainage system of FIG. 2.

FIG. 1 illustrates a conventional intracranial pressure release system 20 much like that disclosed in U.S. Pat. No. 5,772,625 to Krueger, et al. This system 20 operates on hydrostatic pressure and has a drainage catheter 22 with a plurality of drainage apertures 24 on its distal end 28a inserted through a scalp incision 26 of a patient. The drainage catheter 22 has a proximal end 28b that attaches to the top of a fluid column 30. One or more medical connectors disposed between the proximal end 28b and distal end 28a of the drainage catheter 22 provide ports 21 for sampling or infusion, such as sampling port 32. A one-way valve is typically connected to drainage catheter 22 to prevent retrograde flow. The fluid column 30 is height adjustable with respect to a stationary pole 34 and has an outlet 36 in communication with an inlet 38 of a reservoir bag 40 through a three-position stop cock SC. With the stop cock SC open, fluid drains through the catheter 22, the fluid column 30, and into the reservoir bag 40 depending on the elevation of the fluid column relative to the distal end 28a. Thus, the height of the fluid column 30 regulates the pressure differential through the drainage catheter 22.

The system 20 illustrated in FIG. 1 is relatively cumbersome and essentially relegates the patient to the hospital bed. As the pressure within the patient's cranium fluctuates, the height of fluid column 30 must be adjusted to maintain the proper pressure differential through the catheter 22. Moreover, movement of the patient changes the relative elevation of the proximal and distal ends of catheter, and thus alters the pressure differential therethrough. Consequently, a nurse or attendant must move the column each time the patient wishes to move for example for a seated to a lying posture or vice versa. This prior art system is both cumbersome, inconvenient to the patient, and requires a nurse to spend time attending to the patient.

DETAILED DESCRIPTION OF SOME EMBODIMENTS OF THIS INVENTION

One embodiment of the intracranial drainage system 50 of present invention is shown in FIG. 2 mounted to the head 52 of a patient. FIG. 3 shows this system 50 in isolation and partially exploded. The drainage system 50 comprises a drainage catheter 54 having a distal end 54a with a plurality of drainage apertures 56 therein. A proximal end 58 of the drainage catheter 54 is in fluid communication with an inlet 60a of a one-way pressure-responsive valve 60. The proximal end 58 may connect directly to the inlet 60a of the pressure-responsive valve 60, or may be connected via an intermediate three-way junction or stock cock 62 having a sampling port 64. A mating pair of connectors 66 may be utilized so that the drainage catheter 54 can be decoupled from the remainder of the system if necessary.

Figure 10:
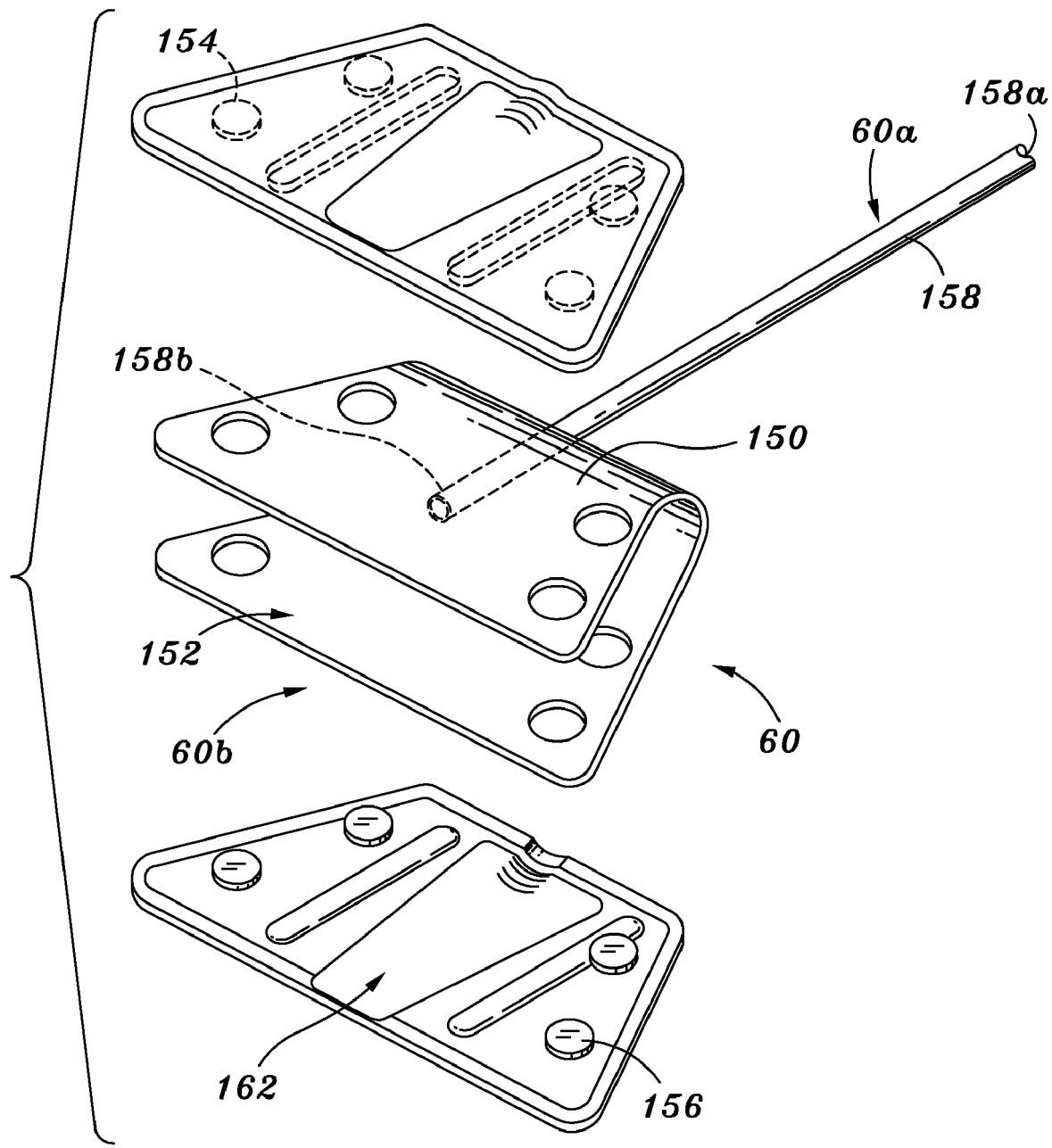
FIG. 10 is an exploded perspective view of the pressure-responsive valve used in the system of this invention.

A drainage tube 70 attaches to an outlet 60b of the pressure-responsive valve 60 and has a coupling 72 on its opposite end that mates with an inlet to 74 of a reservoir bag 76. The system 50 is shown assembled in FIG. 2 and attached to the head 52 of the patient. It can be seen that the proximal end 58 of the drainage catheter 54, the pressure-responsive valve 60, and the inlet tube 74 to the reservoir bag 76 are generally at the same elevation or height above ground level when the patient's head 52 is upright. Specifically, the drainage apertures 56 at the distal end of the catheter 54, the reservoir inlet 74, and the pressure-responsive valve 60, including its inlet 60a and outlet 60b all lie in substantially same plane P and the reservoir inlet 74 and inlet 60a and outlet 60b all lie along the line L which is in the plane P. The pressure at the inlet 60a is the intracranial pressure and the pressure at the outlet 60b is atmospheric. Because the reservoir inlet 74 and the outlet 60b are As shown in FIG. 10 the pressure-responsive valve 60 is designed to be sensitive to changes in pressure to open and close. This valve 60 has an hour shaped resilient membrane 150 folded to form an elongated slit type opening 152 comprising the outlet 60b. The folded membrane 150 is between a pair of plates 154 and 156 that maintain it in tension to normally closed the opening 152. The inlet 60a of the pressure-responsive valve 60 comprises a tube 158 having one end 158a in communication with the proximal end of the catheter 54 through the stop cock 60 and another end 158b in communication with a venturi chamber 162. Preferably, the venturi chamber 162 has a trapezoidal configuration with sidewalls that taper inward at an angle of about 10°. The particulars of such a pressure-responsive valve 60 can be found in U.S. Pat. Nos. 5,071,408 and 5,743,869, both to A. Mateen Ahmed, the disclosures of which are hereby expressly incorporated by reference.

The components of the system 50 are mounted on structure that fits to the patient's head 52 and maintains the components at their respective elevations. More particularly, the head mounting structure is a headband H that includes a horizontal strap 80 having an adjustment buckle 82, and a vertical strap 84 having a length that can be adjusted using mating hook and loop fasteners 86, or other similar expedient. The three-way junction 62 and pressure-responsive valve 60 desirably attach to a rear portion of the horizontal strap 80 as shown. These components, typically made of polymeric material, may be glued, or attached using stitches, or more securely using rivets to the horizontal strap 80. The reservoir bag 76 hangs generally vertically downward from a vertical attachment strap 90 sewn to the horizontal strap 80 with stitching 92. Desirably, the reservoir bag 76 is detachable from the strap 90 such as with a pair of mating snaps 94, 96 on a flange 98 of the reservoir bag and the strap, respectively. Because the coupling 72 on the drainage tube 70 can be disengaged from the inlet tube 74, the reservoir bag 76 can thus be removed when full and replaced with an empty bag. Alternatively, fluid within the reservoir bag 76 may be drained through an outlet tube 100.

With reference again to FIG. 2, the approximate location of the distal end 54a of the drainage catheter 54 after insertion in the cranium is ideally in the plane P, but may be slightly above or below this plane P. The particular location within the patient's head 52 from which fluid must be drained varies, though once inserted, the drainage apertures 56 remain at a substantially fixed elevation with respect to the pressure-responsive valve 60 as long as the patient's head 52 remains stationary. However, even if the patient changes from a sitting to a lying down position, for example, the distances are so small that the relative elevations of the drainage apertures 56 and the pressure-responsive valve 60 remain essentially constant. In other words, the proximal end 58 of the catheter 54, the inlet 60a and outlet 60b of the valve 60, and the inlet 74 of the reservoir 76 are positioned nearby each other so that there is essentially no hydrostatic pressure affecting to flow of fluid from the cavity of a patient. Typically, the distance between the outlet 60b of the valve 60 and the inlet 74 of the reservoir 76 is no greater than about 3 inches. Typically, the proximal end 58 of the catheter 54, the inlet 60a and outlet 60b of the valve 60, and the inlet 74 of the reservoir 76 are at substantially the same height. The positioning minimize any hydrostatic pressure in the system affecting to flow of fluid from the cavity in the cranium of the patient. In a preferred embodiment, the system 50 maintains the drainage apertures 56 at substantially the same elevation as the pressure-responsive valve 60 and the inlet 74 to the reservoir bag 76, so that the drainage apertures 56 at the distal end of the catheter 54, the reservoir inlet 74, and the pressure-responsive valve 60, including its inlet 60a and outlet 60b, all lie in substantially same plane P. Because the relative elevations of these various components of the drainage system 50 are substantially fixed, the system can be calibrated to relieve fluid pressure from within the cranium. That is, the pressure-responsive valve 60 permits fluid flow therethrough upon a predetermined pressure buildup within the drainage catheter 54. The system 50 can be calibrated so that fluid flows through the drainage catheter 54 upon reaching a threshold pressure differential across the pressure-responsive valve 60. In this system, the inlet 60a of the valve 60 is at the internal fluid pressure with the cranium of the patient and the outlet 60b is at atmospheric pressure. The valve 60 is calibrated to open when the differential in pressures between the inlet 60a and the outlet 60b of the valve 60 is at a predetermined level. Below this level the valve automatically closes. In this way, fluid is only removed from the cranium due to abnormal pressures.

As seen in FIGS. 2 and 3, and in more detail in FIGS. 5 and 6, the drainage catheter 54 incorporates an exterior cranium connector-seal 110 thereon. As depicted in FIG. 5 a bore hole 114 is drilled into the cranium 112 and a cranium connector-seal 110 is inserted into this bore hole. The cranium connector-seal 110 has a cylindrical through bore or passageway 124 therein through which passes the drainage catheter 54. The cranium connector-seal 110 is shown isolated in FIG. 6 and includes a generally tubular sleeve 120 with an enlarged flange or head 122 on a proximal end held in position after insertion into the bore hole 114 by sutures 132. The sleeve 120 and head 122 together defined the passageway 124 that receives the exterior of the drainage catheter 54. A medical grade adhesive may be used to fasten the connector-seal 110 to the exterior of the drainage catheter 54. An elongated V-shaped slit 126 may be formed in the sleeve 120 so that passageway 124 can be sized slightly smaller than the catheter 54 and the connector-seal 110 expands to fit over the catheter in an interference fit. In this regard, the cranium connector-seal 110 may be mounted on the catheter 54 merely by a friction fit and does not have to be fastened to the catheter 54 with an adhesive.

The exterior surface of the sleeve 120 tapers inward due to the slit 126 being closed upon inserting the cranium connector-seal 110 into the bore hole 114. There are a series of raised fingers 130 parallel to the longitudinal axis X of the sleeve 120 that assist in gripping the side wall 114a of the bore hole 114. The cranium connector-seal 110 is made of a soft material that fills the annular space between the exterior of the catheter 54 and the cranium bore 114. For example, the connector-seal 110 may be made of a soft silicone, polytetrafluoroethylene (PTFE or Teflon), Dacron, polypropylene, or polyamide. The bore hole 114 may have to be enlarged from holes formed for catheters without the connector-seal 110. The conventional technique is to size the bore hole 114 slightly larger than the catheter and utilize a cementitious material or fibrin glue to fill the annular space. When using the cranium connector-seal 110, the bore hole 114 may be enlarged by 20% or more, from 5 to 7 millimeters (mm) for example. In one embodiment, the cranium connector-seal 110 is formed of two different materials, or at least two different material properties, such that the surface of the passageway 124 is relatively stiffer than the outer surface threads 130. In this way, the connector-seal 110 more securely mounts over the catheter 54, yet still is pliable enough to conform to the generally irregular cranium bore 114.

Figure 11:
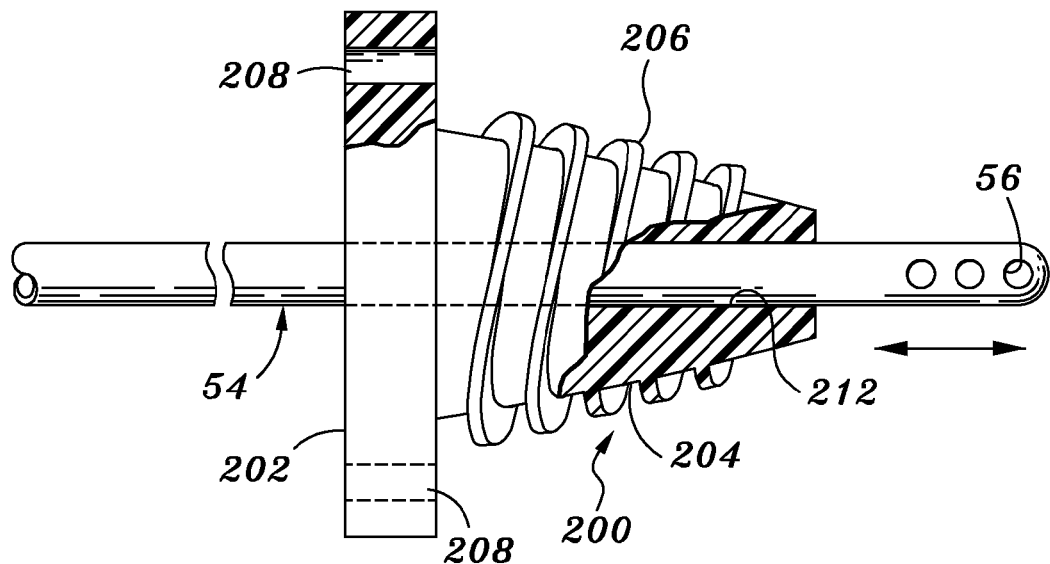
FIG. 11 is a side view with sections broken away showing the plug-type connector used in one embodiment of the system of this invention.
Figure 12:
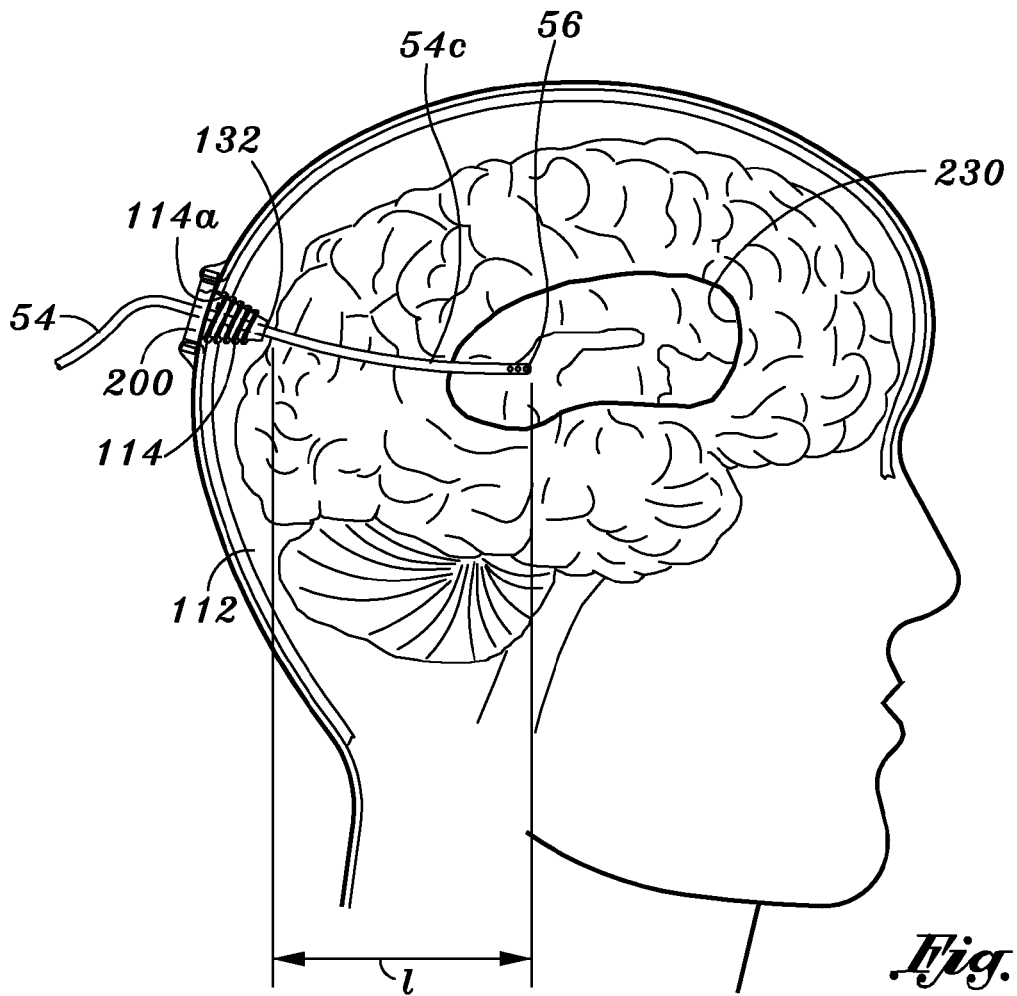
FIG. 12 is a schematic view showing the plug-type connector depicted in FIG. 11 inserted into a bore hole in the cranium of a patient with a distal end lodged within a cavity formed by the ventricle walls of the patient's brain.

FIGS. 11 and 12 depict an alternate cranium connector, the cranium connector-seal 200, which may also may be made of a soft silicone, polytetrafluoroethylene (PTFE or Teflon), Dacron, polypropylene, or polyamide. The cranium connector-seal 200 comprises an enlarged head 202 and a truncated conical body 204 with a helical thread 206 on the exterior surface of the truncated conical body and a passageway 212 through the body 204 for the catheter 54. There are openings 208 in the head 202 that allow the connector-seal 200 to be sutured with sutures 132 (FIG. 12) to the cranium 112 after insertion into the bore hole 114. Prior to inserting the cranium connector-seal 200 into the bore hole 114, the catheter 54 is inserted through passageway 212, limiting the length l of the distal end portion 54c (FIG. 12) of the catheter 54 to about 6 to about 14 inches.

In use, the bore hole 114 is first drilled through the cranium 112. The distal end portion 54c of the catheter 54 having the drainage apertures 56 therein is then inserted through the passageway 212 in the cranium connector-seal 200 and the cranium connector-seal is inserted into the bore hole 114 with the narrow distal end of the conical body 204 fitting into the bore hole 114. Because of the conical shape of the body 204, the distal end of this body fits into the bore hole 114 although its proximal end is sized somewhat larger. When resistance is met, the entire catheter 54 with cranium connector-seal 200 thereon is advanced by gentle rotation so that threads 206 engage the side wall 114a of the bore hole 114. As with any such operation, the threads 206 help advance the connector-seal 200 into the bore hole 114. The head 202 may be provided with flats with which a wrench or other such tool may engage to help seat the cranium connector-seal 200 into the bore hole 114. Eventually, the head 202 abuts the exterior of the cranium 112, and the sutures 132 may be sewn to the cranium 112 to prevent reverse rotation. Because a secure and fluid tight seal is thus created, there is no leakage around the catheter 54. This means the intracranial pressure is more accurately transmitted without loss through the catheter 54. This results in a more consistent and accurate regulation of the fluid flow through the pressure-responsive valve 60.

It should be noted that the length of the catheter 54 that extends through the cranium (i.e., is distal end portion 54c to the cranium connector-seal 200) is shorter than prior art systems. Many systems have no positive depth gauge, as the catheter-mounted connector-seal 200 provides, and may be inserted up to 9 inches into the cranial space. Consequently, the catheter may touch brain tissue and induce growth of such tissue onto the apertures 56 of the catheter 54. The present invention, on the other hand, avoids or reduces the likelihood of this problem, because the pressure within the cavity keeps the ventricle walls 230 (FIG. 12) from touching the distal end portion 54c of the catheter 54. The present invention also employs a relatively short length of the catheter 54 distal to the connector-seal 200, for instance only about 3.5 inches in most cases.

FIG. 7 illustrates an alternative self-sealing catheter 140 for insertion through a bore hole in a cranium 142. As before, the catheter 140 includes an elongated hollow tube 144 preferably having a plurality of drainage apertures 146 on its distal end. The catheter 140 further includes a relatively soft helical sealing member 148 on its exterior and extending an axial length adjacent the distal end. In an exemplary embodiment, the sealing member 148 comprises a soft silicone rib that attaches to and projects outward from the catheter tube 144. The rib 148 may be attached using heat or ultrasonic welding. By sizing the bore hole through the cranium 142 just slightly larger than the diameter of the tube 144, an interference fit is created between the outwardly projecting sealing member 148 and the side wall of bore hole. Because of its helical arrangement, the sealing member 148 acts as a thread of sorts that helps advance the catheter 140 into sealing engagement with the bore hole.

Figure 8:
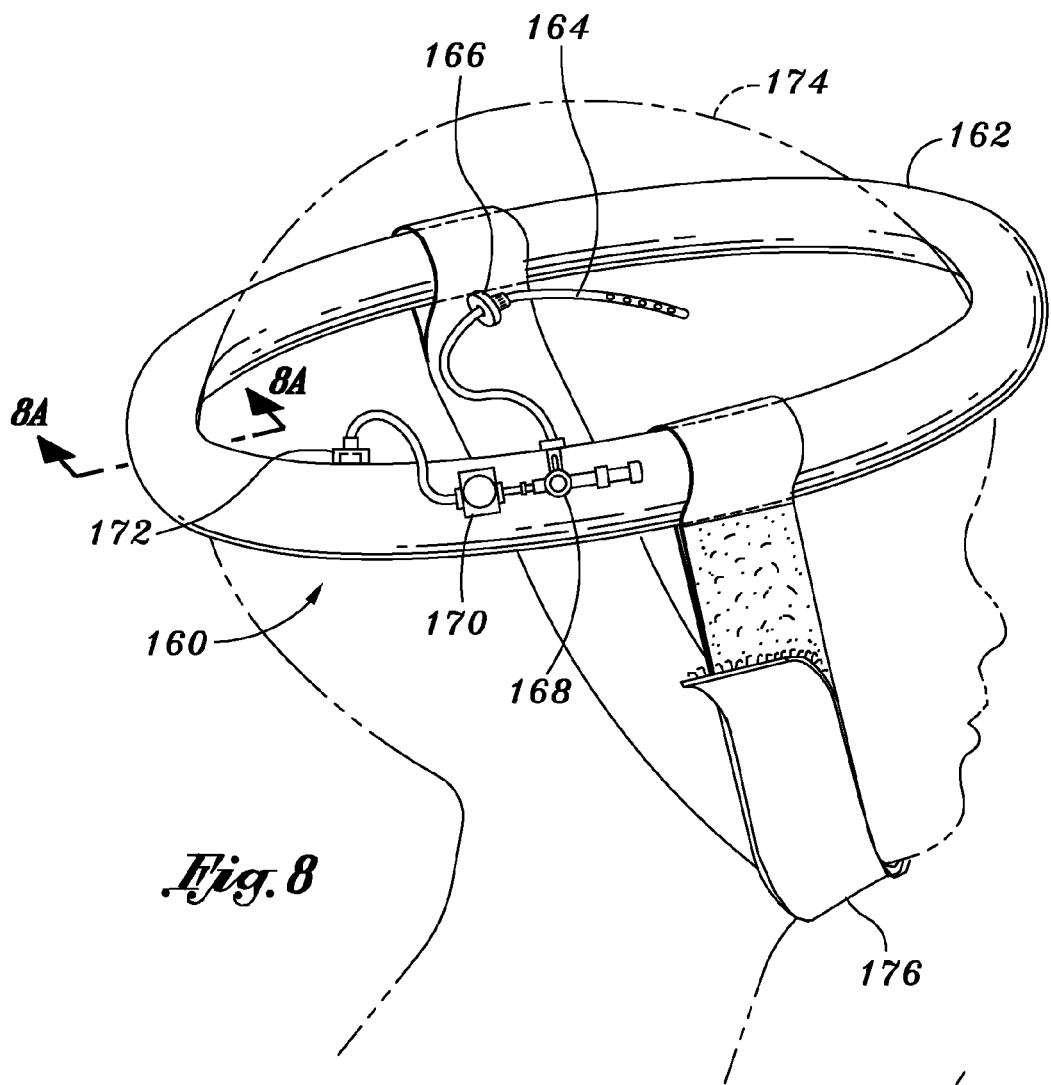
FIG. 8 is a perspective view of an alternative external intracranial drainage system of the present invention having a tubular reservoir and mounted on the head of a patient (shown in phantom)
Figure 8A:
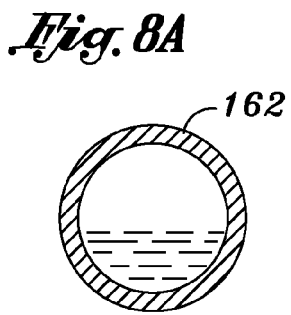
FIG. 8A is a cross-sectional view through the tubular reservoir taken along line 8A-8A of FIG. 8.

An alternative external drainage system 160 of the present invention shown in FIG. 8 replaces the conventional reservoir bag with a hoop-shaped reservoir 162. As before, the system 160 includes a drainage catheter 164 having a cranium seal 166 thereon and connected at a proximal end to a stop cock or three-way port 168. A pressure-responsive one-way valve 170 similar to that shown in FIG. 10 is positioned in the fluid flow line between the three-way port 168 and an inlet 172 to the reservoir 162. The reservoir 162, seen in cross-section in FIG. 8A, is sized to rest horizontally on the patient's head 174. For this purpose, several sizes of reservoir 162 may be made available. An adjustable vertical strap 176 is secured with loops on either side of the reservoir 162 to secure the system 160 in place. The hoop-shaped reservoir 162 is somewhat less cumbersome than a conventional reservoir bag as described above. As in the earlier-described embodiment, the relative elevations of the drainage catheter 164, one-way valve 170, and reservoir inlet 172 remain fixed in essentially the same plane even upon movement of the patient's head.

Figure 9A:
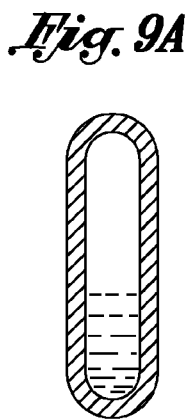
FIG. 9A is a cross-sectional view through the annular reservoir taken along line 9A-9A of FIG. 9.
Figure 9:
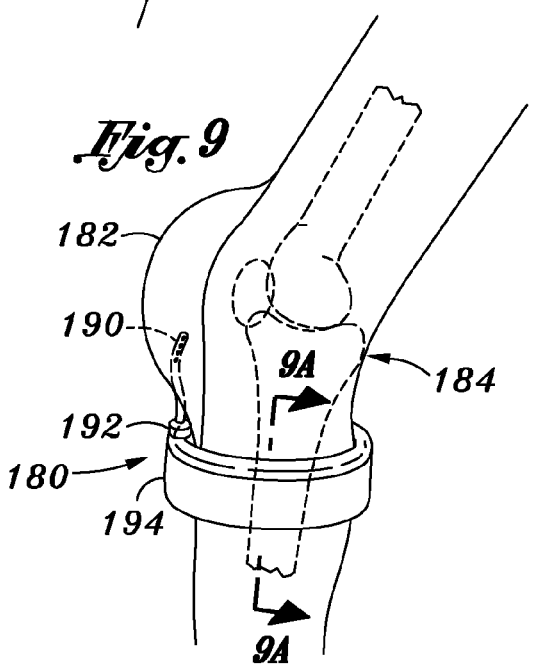
FIG. 9 is a perspective view of an external drainage system of the present invention having an annular reservoir and mounted for drainage of a swollen knee.

FIGS. 9 and 9A illustrates a drainage system 180 of the present invention in use in a location other than the cranium, in particular to remove fluid swelling 182 from the knee joint 184. The system 180 includes a drainage catheter 190 in fluid communication with an inlet 192 of an annular reservoir 194. Although not shown, a pressure-responsive one-valve will be positioned in series between the drainage catheter 190 and the reservoir 194. The reservoir 194 is illustrated in cross-section FIG. 9A and is desirably shaped in a narrow oval so as to have a lower profile around the leg and be less conspicuous when worn beneath pants. Once again, the proximity of the components of the system 180 means that their relative elevations are substantially the same, which provides consistent static pressure differentials across the one-way valve.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention:

The invention claimed is:

1. A system for relieving fluid pressure from a body cavity of a patient comprising a drainage catheter for insertion into the body cavity, said catheter having an outlet end and an inlet end including at least one drainage aperture, said inlet end adapted to be inserted into the cavity at a predetermined position within the cavity with said outlet end extending from the body cavity, a one-way pressure-responsive valve that opens when the differential between atmospheric pressure and the pressure within the body cavity exceeds a predetermined difference and closes when said differential is less than said predetermined difference, said valve having an outlet and an inlet in fluid communication with the outlet end of the drainage catheter to permit pressure-regulated flow of fluid from the body cavity through the catheter, said outlet of the pressure-responsive valve being at substantially atmospheric pressure and the inlet of the pressure-responsive valve being at the pressure within the body cavity, a reservoir having an inlet in fluid communication with the outlet of the pressure-responsive valve so as to receive the fluid that passes therethrough, and a mounting member adapted to be detachably coupled to the patient nearby the body cavity, said drainage catheter, pressure-responsive valve, and reservoir being configured to be attached to the mounting member in predetermined fixed positions relative to each other where the inlet end of the drainage catheter, the inlet and outlet of the pressure-responsive valve, and the inlet of the reservoir all lie in substantially the same plane so essentially no hydrostatic pressure affects the flow of fluid from the cavity of the patient even with changing positions of the patient, wherein the body cavity is within the cranium and the mounting member comprises a headband adapted to be wrapped around the head of the patient.

2. The system of claim 1 where the headband includes
a first component sized to fit around the circumference of the patient's head, and
a second component connected by opposed ends thereof to the first component and sized to fit over the top of the patient's head.

3. The system of claim 1 where the headband includes a releasable chin strap to permit easy removal.

4. The system of claim 1 where the first component is adjustable to different patient head circumferences.

5. The system of claim 1 where the headband comprises at least a partially hollow member that functions as the reservoir.

6. The system of claim 5 where the hollow member is hoop-shaped.

7. The system of claim 1 where the reservoir is detachably connected to the headband.

8. The system of claim 7 where the headband and reservoir are connected by a snap-type connector.

9. A system for relieving fluid pressure resulting from the fluid collecting in a cavity in the body of a patient, said system comprising
a mounting member adapted to be attached to the body of the patient,
a drainage catheter, a one-way pressure-responsive valve, and a reservoir all adapted to be detachably connected to the mounting member, and
means for connecting to the mounting member in fixed positions relative to each other the catheter, valve, and reservoir so, when the system is operating, said catheter, valve, and reservoir are configured to enable the patient can change positions essentially without creating a substantial hydrostatic pressure change in the system.

10. A system for relieving fluid pressure resulting from the fluid collecting in a cavity in the cranium of a patient, said system comprising
a mounting member adapted to be attached to the head of the patient,
a drainage catheter, a one-way pressure-responsive valve, and a reservoir all adapted to be detachably connected to the mounting member in fixed positions relative to each other when the system is operable,
said drainage catheter having an outlet end and an inlet end including at least one drainage aperture, said catheter adapted to be inserted into the cavity at a predetermined position within the cavity with said outlet end extending from the cavity and the drainage aperture within the cavity in a substantially fixed position,
said one-way pressure-responsive valve having an outlet and an inlet in fluid communication with the outlet end of the drainage catheter to permit pressure-regulated flow of fluid from the cavity through the catheter, said outlet of the valve being at substantially atmospheric pressure and the inlet of the valve being at the pressure within the body cavity, said valve opening when the differential between atmospheric pressure and the pressure within the cavity exceeds a predetermined difference and closes when said differential is less than said predetermined difference,
said reservoir having an inlet in fluid communication with the outlet of the pressure-responsive valve so as to receive the fluid that passes therethrough,
said drainage catheter, pressure-responsive valve, and reservoir being configured to be attached to the mounting member in said fixed positions relative to each other where the inlet end of the drainage catheter, the inlet and outlet of the pressure-responsive valve, and the inlet of the reservoir all lie in substantially the same plane and said drainage aperture remains in said substantially fixed position so, with changing positions of the patient, the relative positions of the drainage aperture and the pressure-responsive valve remain essentially constant.

* * * * *